United States Patent
Lam et al.

(10) Patent No.: US 9,498,386 B2
(45) Date of Patent: Nov. 22, 2016

(54) METHOD OF MAKING DISPOSABLE ABSORBENT DIAPER PANTS

(75) Inventors: Joseph Hung Lam, Ho Chi Minh (VN); Gary Dean Lavon, Liberty Township, OH (US); Ronald Joseph Zink, II, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 815 days.

(21) Appl. No.: 13/221,224

(22) Filed: Aug. 30, 2011

(65) Prior Publication Data
US 2012/0065043 A1    Mar. 15, 2012

Related U.S. Application Data

(60) Provisional application No. 61/381,459, filed on Sep. 10, 2010.

(51) Int. Cl.
*B32B 37/02*     (2006.01)
*A61F 13/15*     (2006.01)

(52) U.S. Cl.
CPC ... *A61F 13/15804* (2013.01); *A61F 13/15699* (2013.01); *A61F 13/15723* (2013.01); *A61F 13/15756* (2013.01)

(58) Field of Classification Search
USPC ...... 156/227, 160, 164, 204, 24.224, 66, 65, 156/266, 304.1, 515, 516, 259
See application file for complete search history.

(56) References Cited

U.S. PATENT DOCUMENTS

| | | | |
|---|---|---|---|
| 3,772,120 A | 11/1973 | Radzins | |
| 3,848,594 A | 11/1974 | Buell | |
| 3,860,003 A | 1/1975 | Buell | |
| 4,610,678 A | 9/1986 | Weisman et al. | |
| 4,662,875 A | 5/1987 | Hirotsu | |
| 4,673,402 A | 6/1987 | Weisman et al. | |
| 4,695,278 A | 9/1987 | Lawson | |
| 4,704,115 A | 11/1987 | Buell | |
| 4,735,673 A * | 4/1988 | Piron | 156/496 |
| 4,775,375 A | 10/1988 | Aledo | |
| 4,795,454 A | 1/1989 | Dragoo | |

(Continued)

OTHER PUBLICATIONS

PCT International Search Report dated Feb. 23, 2012, 11 pages.

*Primary Examiner* — Michael N Orlando
*Assistant Examiner* — Marta Dulko
(74) *Attorney, Agent, or Firm* — Charles R. Matson

(57) ABSTRACT

Aspects of the methods according to the present disclosure relate to the fabrication of diaper pants wherein discrete chassis are advanced in a machine direction such that the longitudinal axis is parallel with the machine direction. Discrete lengths of elastic belt materials are then connected with the first waist region of a first advancing chassis and the second waist region of a second advancing chassis. The lengths of elastic belt materials are cut along the cross-direction between the discrete chassis forming a first elastic belt and a second elastic belt; the chassis are subsequently folded; and the first and second elastic belts disposed on the chassis are bonded together to create a discrete diaper pant. This apparatus and process configuration forms a continuous web of articles formed by intermittently spaced chassis and intermittently spaced elastic belts bridging the gap between the intermittently spaced chassis.

7 Claims, 12 Drawing Sheets

(56) References Cited

U.S. PATENT DOCUMENTS

| | | | |
|---|---|---|---|
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 4,940,464 A | 7/1990 | Van Gompel | |
| 4,946,527 A | 8/1990 | Battrell | |
| 4,950,264 A | 8/1990 | Osborn | |
| 5,092,861 A | 3/1992 | Nomura | |
| 5,151,092 A | 9/1992 | Buell | |
| 5,221,274 A | 6/1993 | Buell | |
| 5,246,433 A | 9/1993 | Hasse | |
| 5,366,782 A | 11/1994 | Curro | |
| 5,429,694 A * | 7/1995 | Herrmann | 156/164 |
| 5,518,801 A | 5/1996 | Chappell et al. | |
| 5,562,646 A | 10/1996 | Goldman et al. | |
| 5,569,234 A | 10/1996 | Buell | |
| 5,599,335 A | 2/1997 | Goldman et al. | |
| 5,607,537 A | 3/1997 | Johnson et al. | |
| 5,622,589 A | 4/1997 | Johnson et al. | |
| 5,628,097 A | 5/1997 | Benson et al. | |
| 5,662,638 A | 9/1997 | Johnson et al. | |
| 5,669,894 A | 9/1997 | Goldman et al. | |
| 5,691,035 A | 11/1997 | Chappell et al. | |
| 5,723,087 A | 3/1998 | Chappell et al. | |
| 5,772,825 A | 6/1998 | Schmitz | |
| 5,779,831 A | 7/1998 | Schmitz | |
| 5,891,544 A | 4/1999 | Chappell et al. | |
| 5,897,545 A | 4/1999 | Kline | |
| 5,916,661 A | 6/1999 | Benson et al. | |
| 5,957,908 A | 9/1999 | Kline | |
| 5,968,029 A | 10/1999 | Chappell et al. | |
| 5,993,432 A | 11/1999 | Lodge et al. | |
| 6,017,406 A | 1/2000 | Vogt | |
| 6,042,673 A | 3/2000 | Johnson et al. | |
| 6,107,539 A | 8/2000 | Palumbo et al. | |
| 6,113,717 A * | 9/2000 | Vogt et al. | 156/73.1 |
| 6,120,487 A | 9/2000 | Ashton | |
| 6,120,489 A | 9/2000 | Johnson | |
| 6,251,097 B1 | 6/2001 | Kline | |
| 6,352,607 B1 * | 3/2002 | Kuen et al. | 156/227 |
| 6,432,098 B1 | 8/2002 | Kline | |
| 6,497,032 B2 * | 12/2002 | Maxton et al. | 29/429 |
| 6,545,197 B1 | 4/2003 | Muller et al. | |
| 6,596,107 B2 * | 7/2003 | Stopher | 156/66 |
| 6,620,276 B1 | 9/2003 | Kuntze et al. | |
| 6,648,869 B1 | 11/2003 | Gillies et al. | |
| 6,669,618 B2 | 12/2003 | Reising | |
| 6,723,035 B2 | 4/2004 | Franklin et al. | |
| 6,726,792 B1 | 4/2004 | Johnson et al. | |
| 6,776,316 B2 | 8/2004 | Van Eperen et al. | |
| 6,790,798 B1 | 9/2004 | Suzuki et al. | |
| 6,830,800 B2 | 12/2004 | Curro et al. | |
| 6,915,829 B2 * | 7/2005 | Popp et al. | 156/519 |
| 6,962,578 B1 | 11/2005 | LaVon | |
| 7,172,585 B2 * | 2/2007 | Sandin et al. | 604/385.3 |
| 7,270,861 B2 | 9/2007 | Broering et al. | |
| 7,341,579 B2 | 3/2008 | Kinoshita | |
| 7,361,167 B2 | 4/2008 | Erickson et al. | |
| 7,390,373 B2 * | 6/2008 | Karlsson et al. | 156/204 |
| 7,569,039 B2 | 8/2009 | Matsuda et al. | |
| 7,587,966 B2 * | 9/2009 | Nakakado et al. | 83/37 |
| 7,799,006 B2 | 9/2010 | Kline | |
| 7,828,783 B2 | 11/2010 | Erickson et al. | |
| 7,975,584 B2 * | 7/2011 | McCabe | 83/343 |
| 2002/0002358 A1 * | 1/2002 | Durrance et al. | 604/385.01 |
| 2002/0119878 A1 * | 8/2002 | Stopher | 493/374 |
| 2003/0088220 A1 | 5/2003 | Molander | |
| 2003/0131943 A1 * | 7/2003 | Frederisy | 156/538 |
| 2003/0205312 A1 * | 11/2003 | Tomsovic et al. | 156/227 |
| 2003/0233082 A1 | 12/2003 | Kline | |
| 2004/0030318 A1 * | 2/2004 | Karlsson et al. | 604/387 |
| 2004/0089403 A1 * | 5/2004 | Satoh | 156/160 |
| 2004/0097895 A1 | 5/2004 | Busam et al. | |
| 2004/0158212 A1 | 8/2004 | Ponomarenko et al. | |
| 2004/0243083 A1 * | 12/2004 | Matsuda et al. | 604/385.01 |
| 2005/0107764 A1 | 5/2005 | Matsuda et al. | |
| 2005/0130821 A1 | 6/2005 | Reising | |
| 2005/0215970 A1 | 9/2005 | Kline | |
| 2005/0215971 A1 | 9/2005 | Roe | |
| 2005/0234419 A1 | 10/2005 | Kline | |
| 2006/0108054 A1 | 5/2006 | Ukegawa | |
| 2007/0074381 A1 | 4/2007 | Raycheck | |
| 2007/0078426 A1 | 4/2007 | Kline | |
| 2007/0078427 A1 | 4/2007 | Raycheck | |
| 2007/0142808 A1 * | 6/2007 | Wada et al. | 604/385.3 |
| 2008/0083489 A1 | 4/2008 | Schneider et al. | |
| 2008/0099130 A1 * | 5/2008 | Umebayashi et al. | 156/191 |
| 2008/0107861 A1 | 5/2008 | Dalal | |
| 2008/0208156 A1 | 8/2008 | LaVon | |
| 2008/0234649 A1 | 9/2008 | Hamall | |
| 2009/0084497 A1 * | 4/2009 | Hornung et al. | 156/297 |
| 2009/0094941 A1 | 4/2009 | Burns, Jr. et al. | |
| 2009/0098995 A1 | 4/2009 | Burns, Jr. et al. | |
| 2009/0312730 A1 | 12/2009 | LaVon et al. | |
| 2009/0312732 A1 | 12/2009 | LaVon | |
| 2009/0312735 A1 | 12/2009 | LaVon | |
| 2009/0312737 A1 | 12/2009 | LaVon | |
| 2009/0312738 A1 | 12/2009 | LaVon | |
| 2010/0049155 A1 | 2/2010 | Söderbergh et al. | |

* cited by examiner

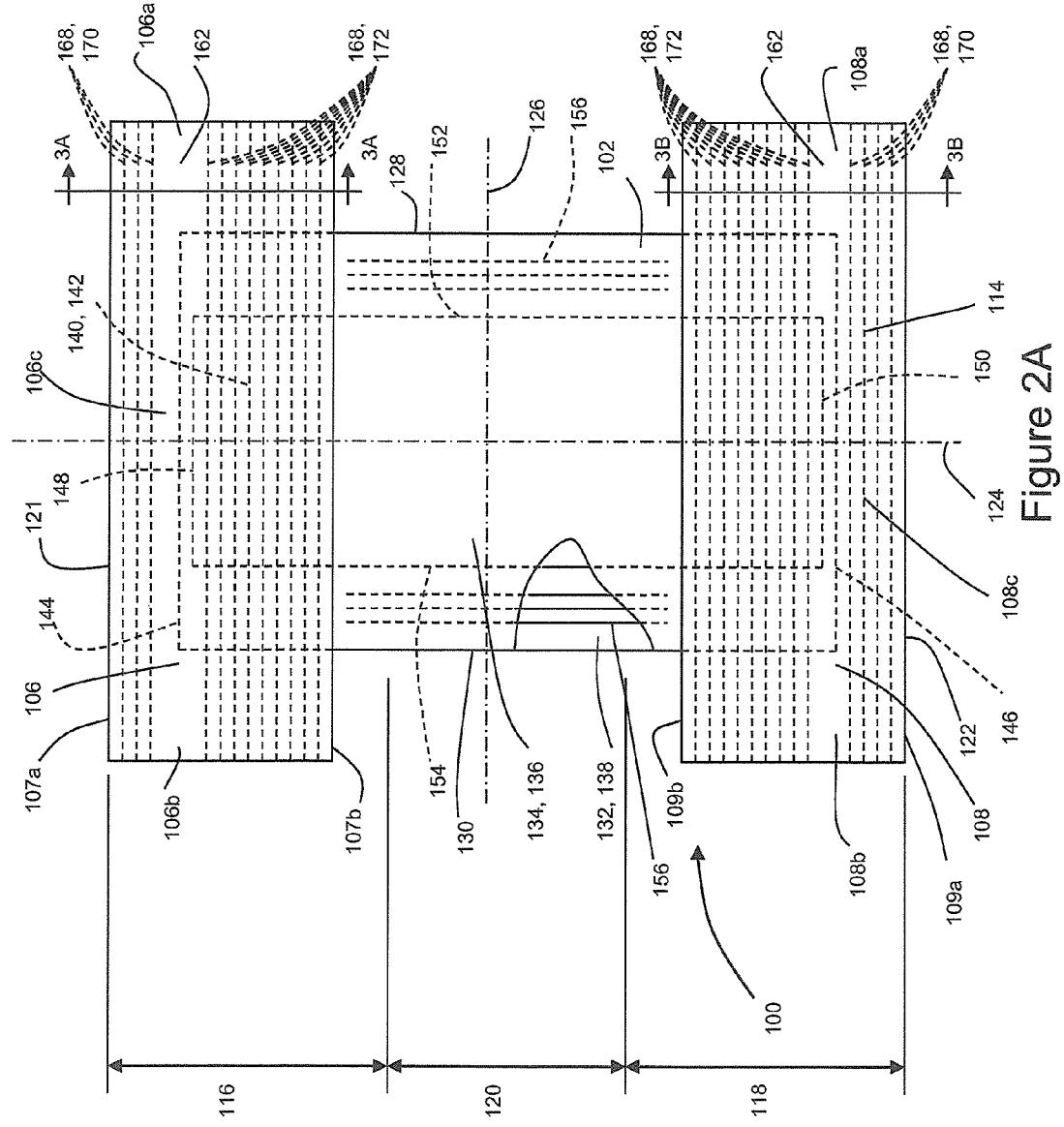
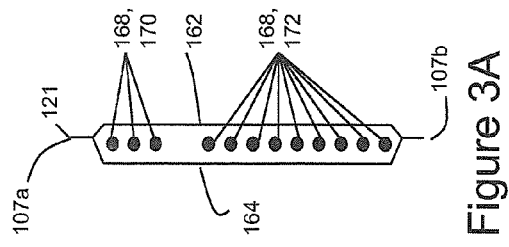
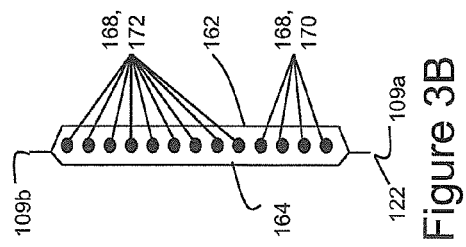

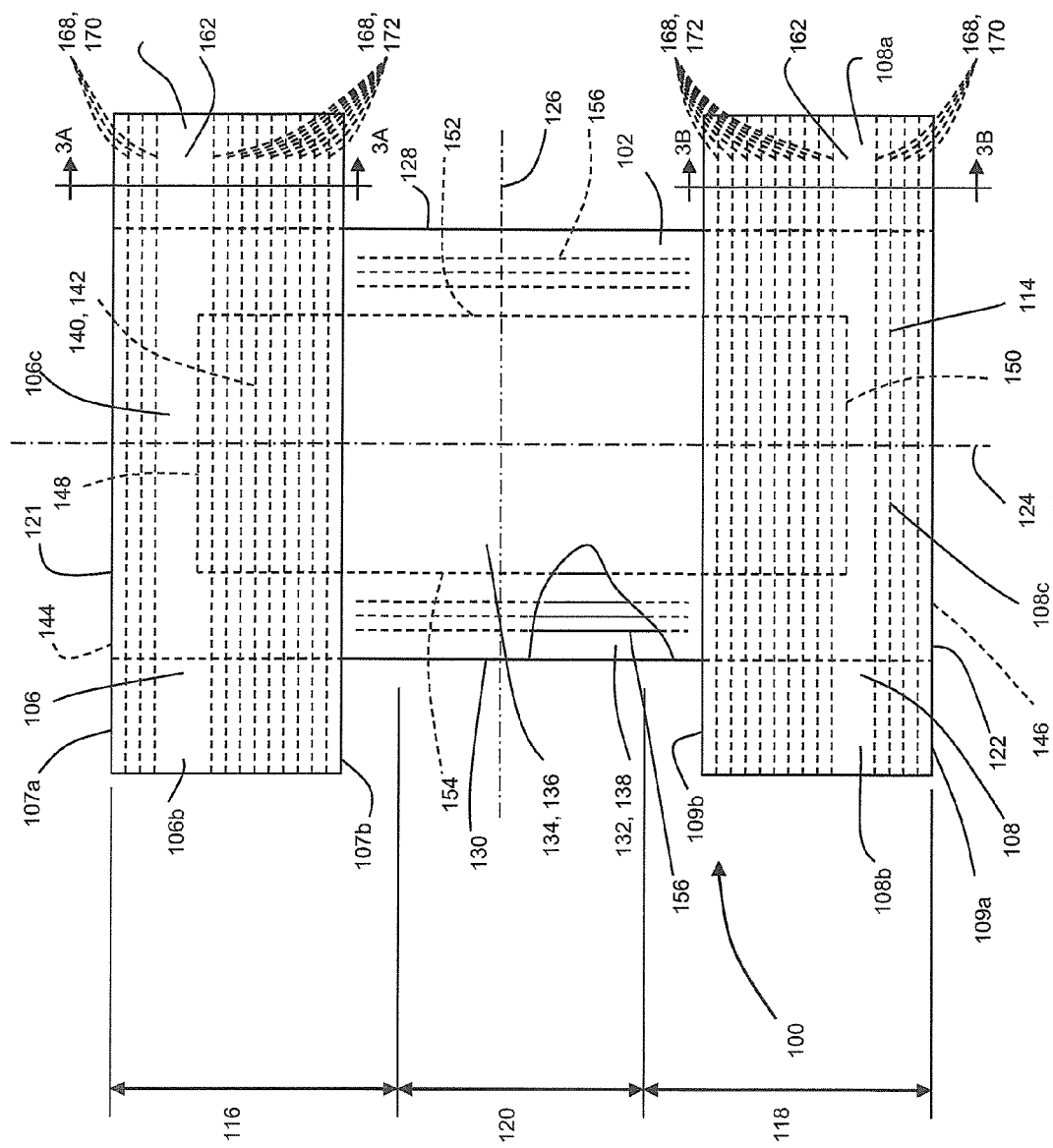

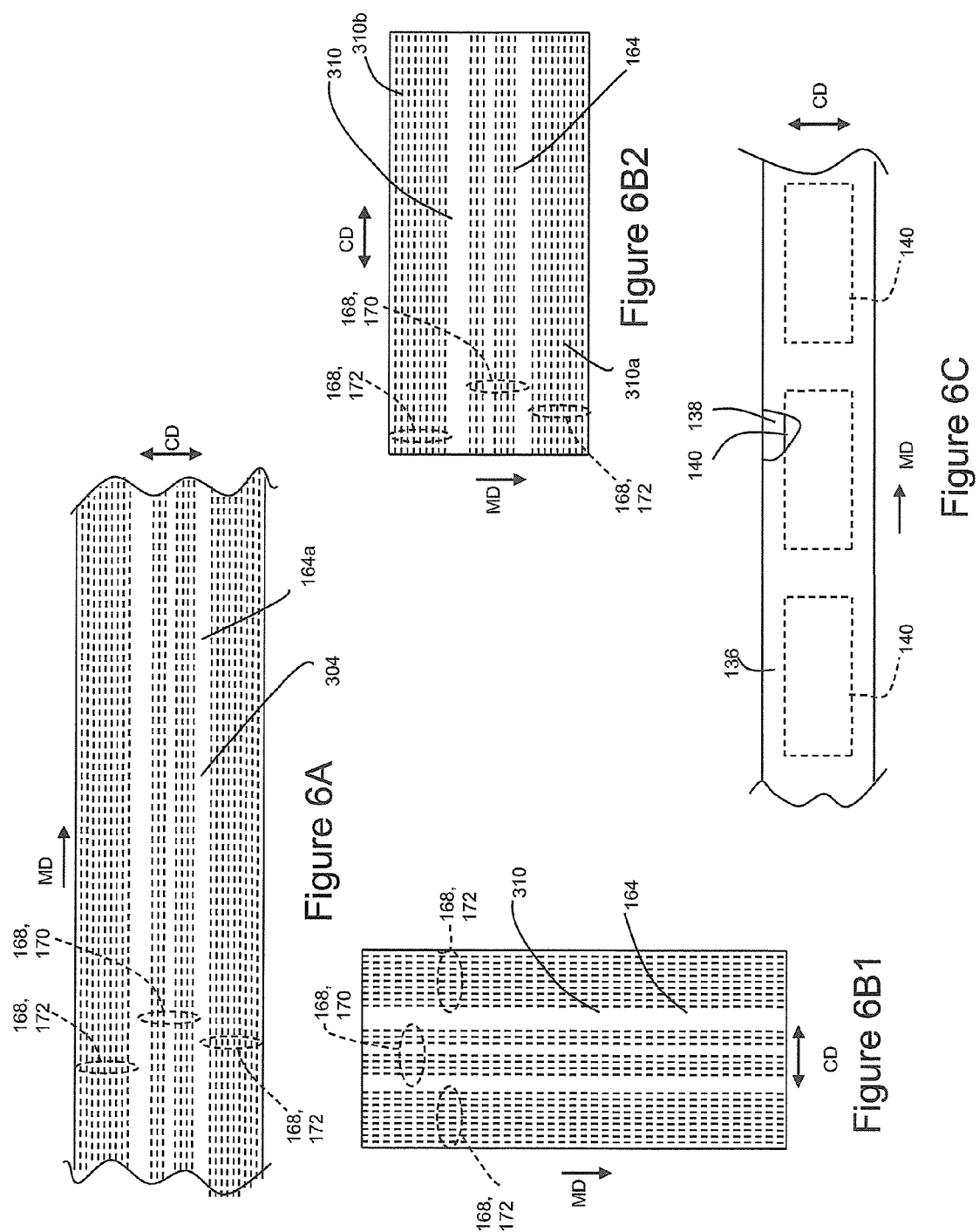

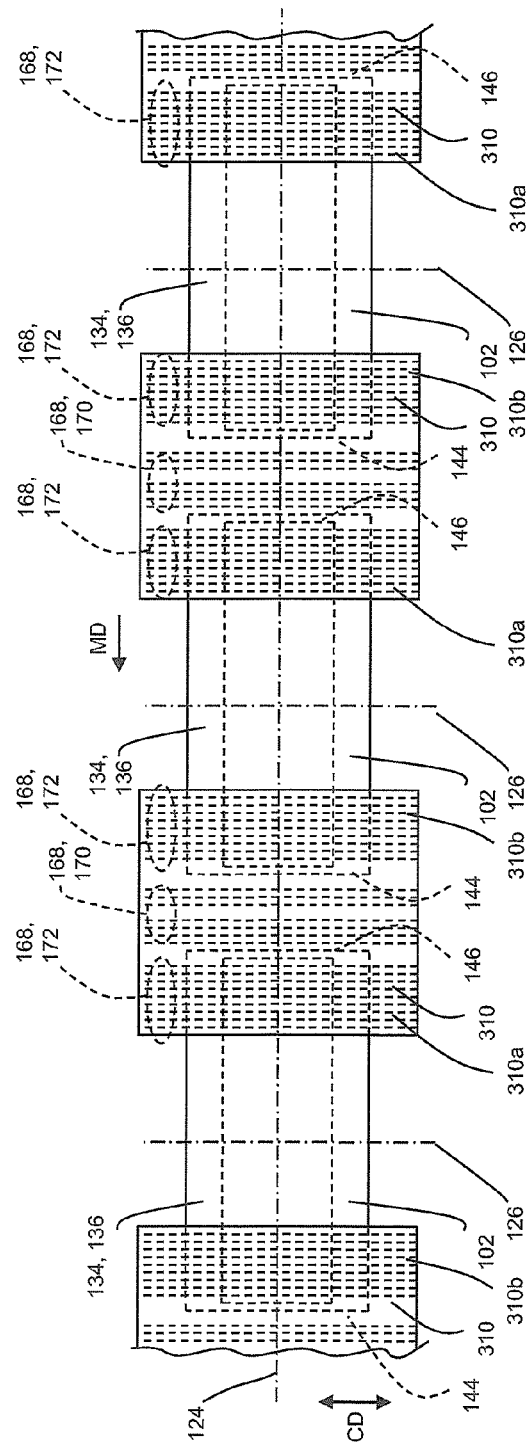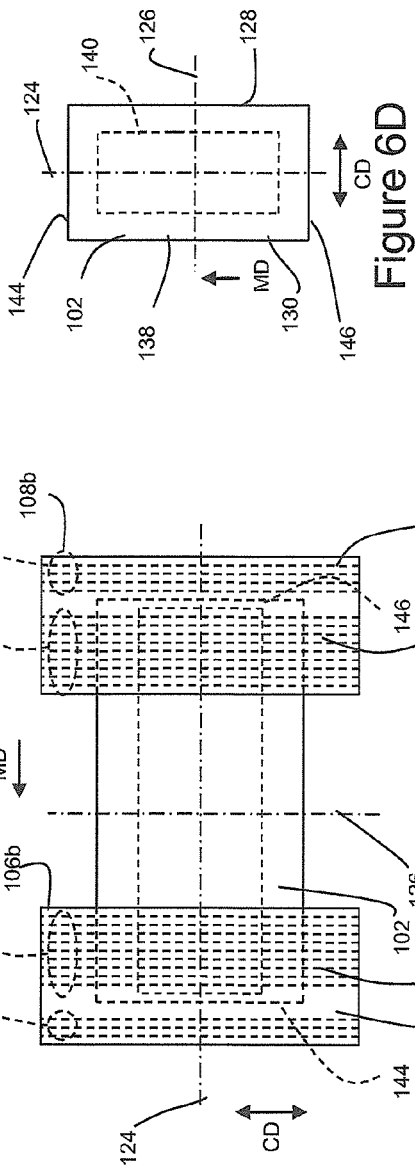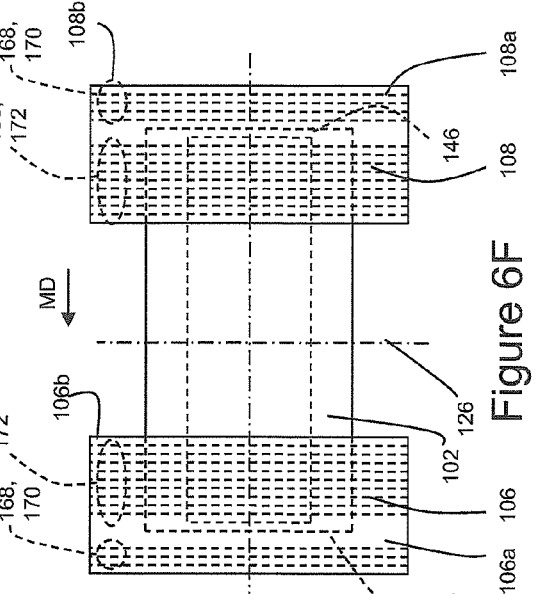

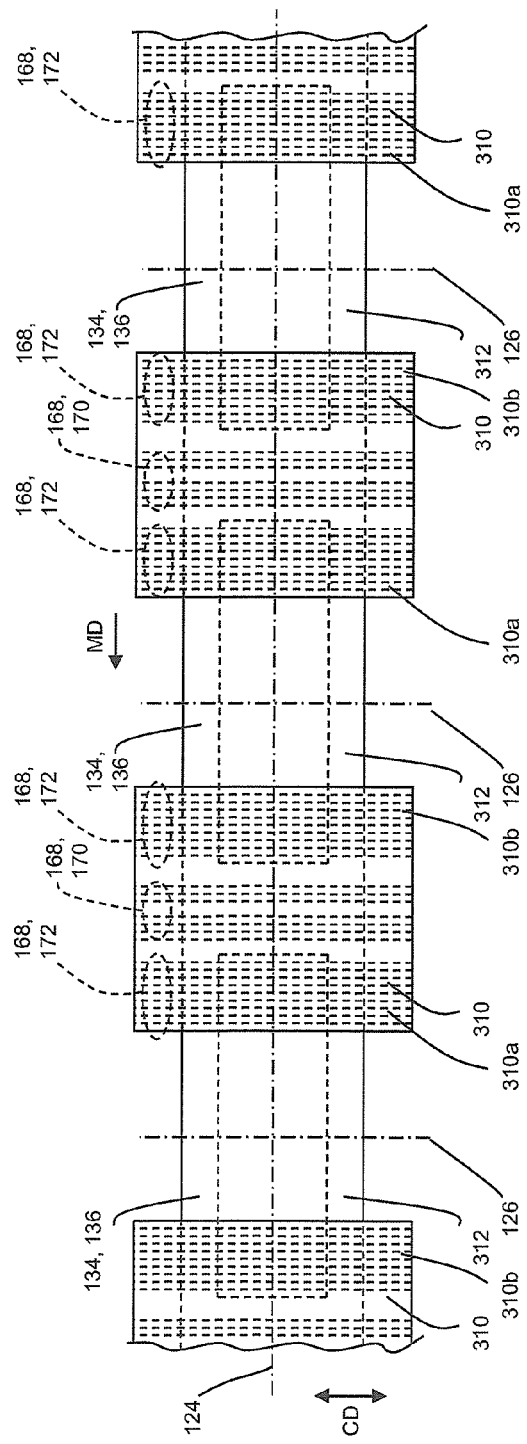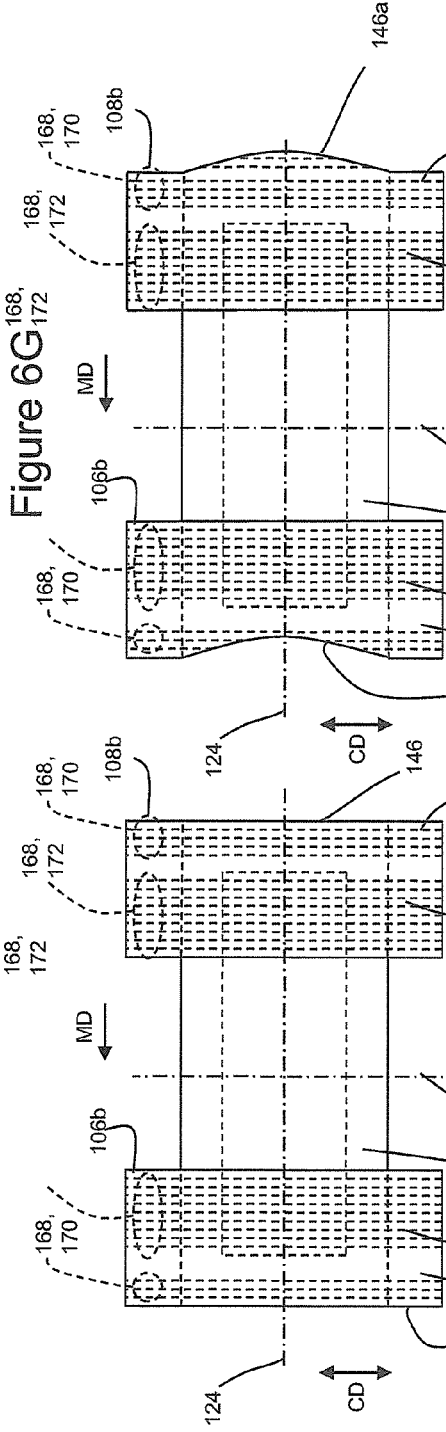

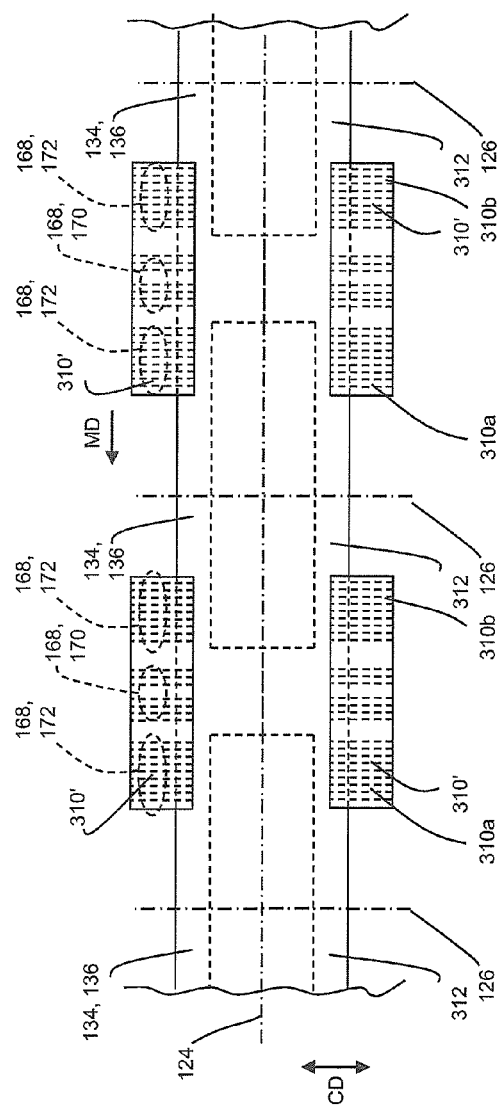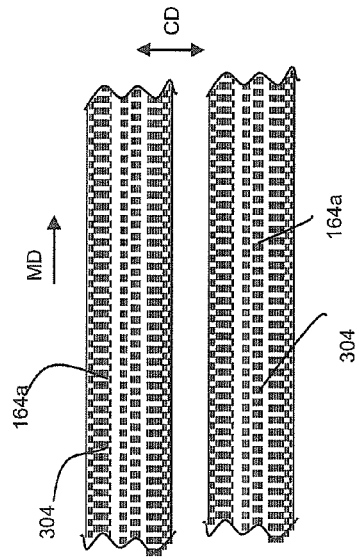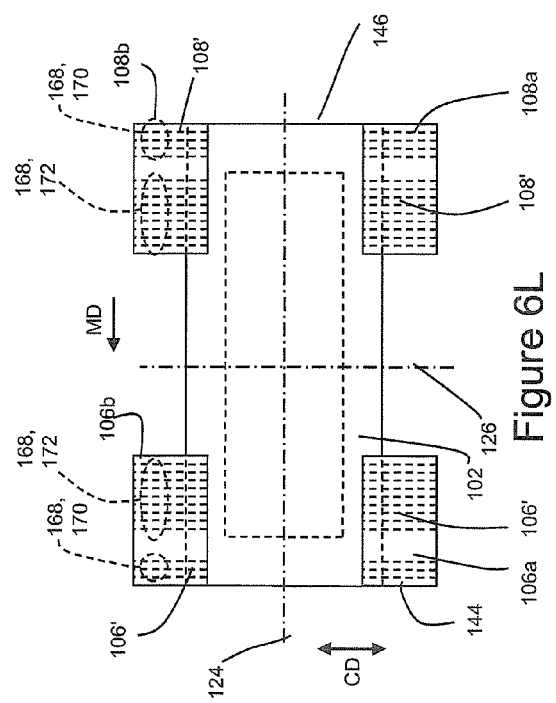

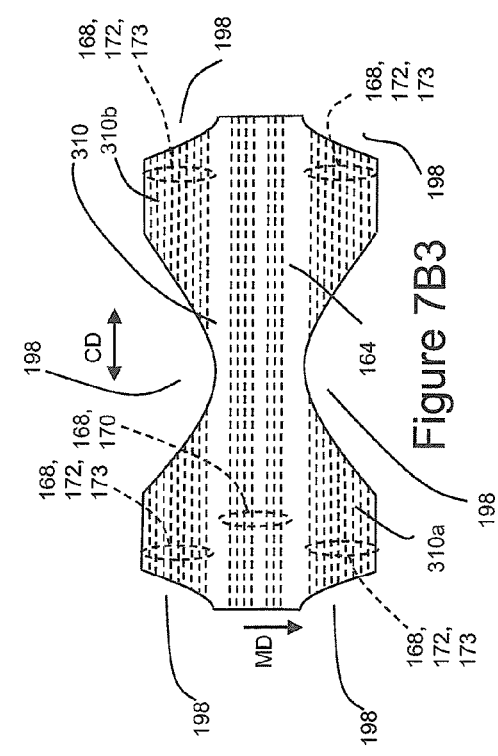
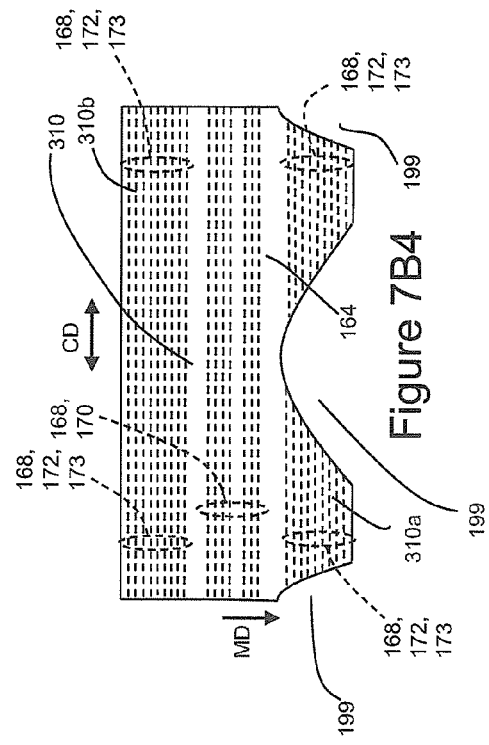
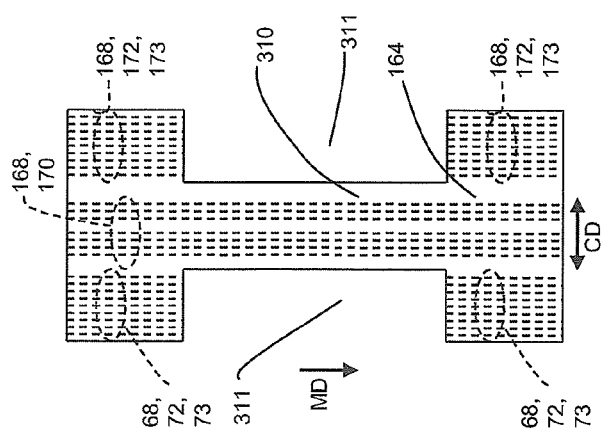
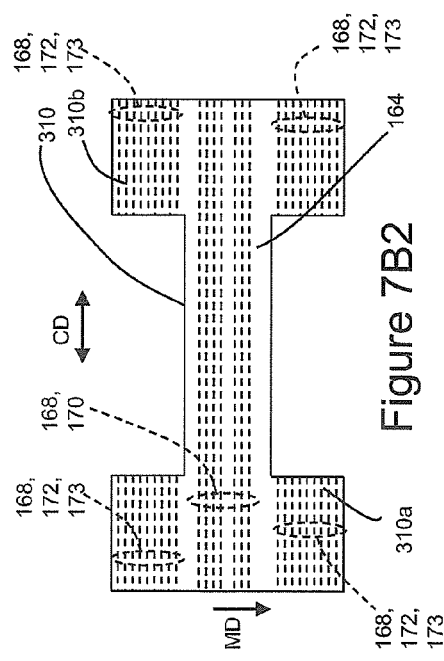

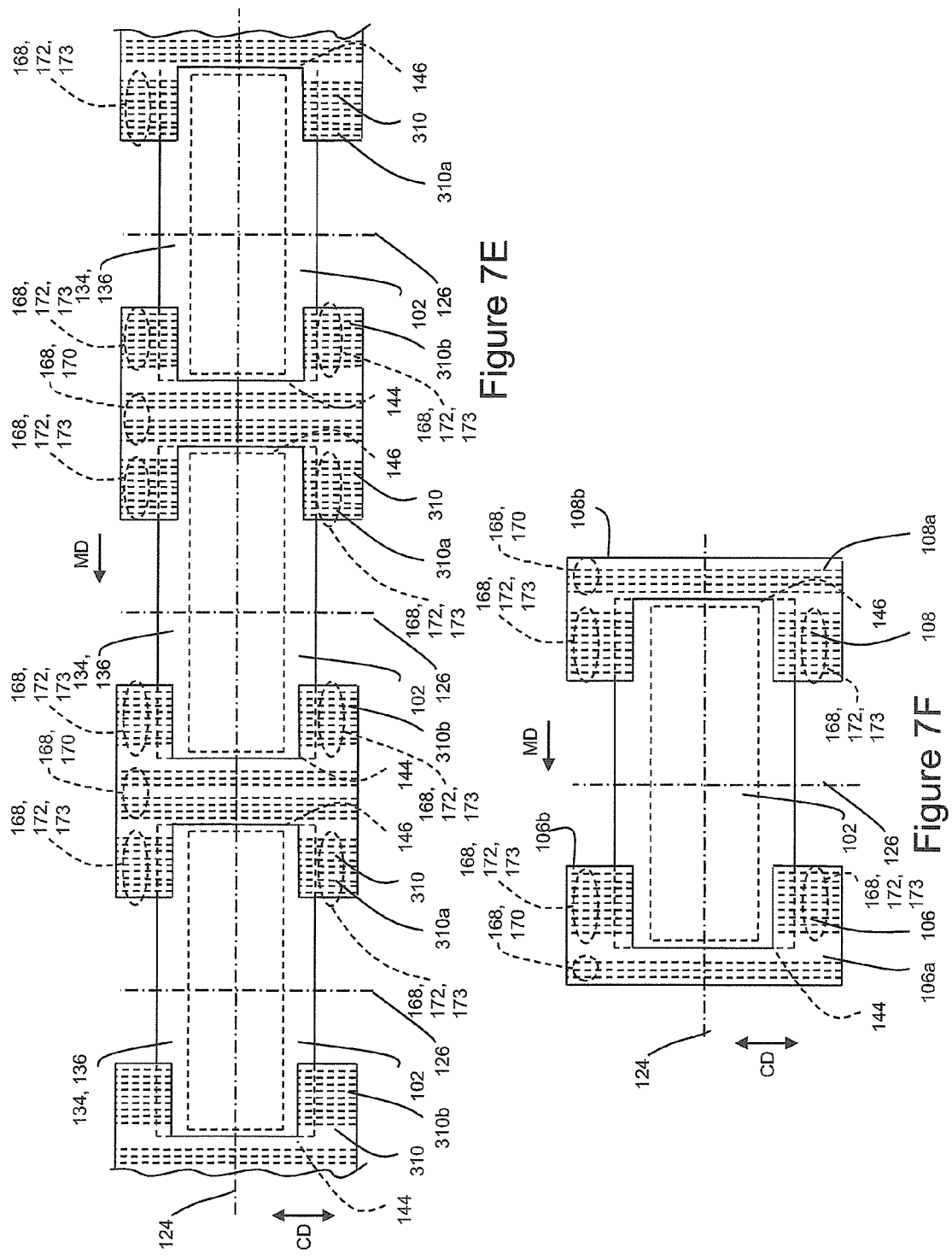

METHOD OF MAKING DISPOSABLE ABSORBENT DIAPER PANTS

CROSS REFERENCE TO RELATED APPLICATION

This application claims the benefit of U.S. Provisional Application No. 61/381,459, filed on Sep. 10, 2010, which is incorporated herein by reference.

FIELD OF THE INVENTION

The present disclosure relates to methods for manufacturing absorbent articles, and more particularly, to methods for making diaper pants having a ring-like elastic belt.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist caps, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis perpendicular with the cross direction. Opposing waist regions of discrete chassis are then connected with continuous lengths of elastically extendable front and back belts advancing in the machine direction. The front and back belts span the spacing between the discrete chassis and as such, form a continuous web of absorbent articles which can be controlled more easily to allow for more accurate registration and phasing of subsequent converting operations, such as folding, seaming, and cutting.

SUMMARY OF THE INVENTION

The present disclosure relates to methods for manufacturing absorbent articles, and in particular, methods for making diaper pants. Aspects of the methods according to the present disclosure relate to the fabrication of diaper pants wherein discrete chassis are advanced in a machine direction such that the longitudinal axis is parallel with the machine direction. Discrete lengths of elastic belt materials are then connected with the first waist region of a first advancing chassis and the second waist region of a second advancing chassis forming a continuous web of articles formed by the intermittently spaced chassis and intermittently spaced elastic belts bridging the gap between the intermittently spaced chassis. The lengths of elastic belt materials are cut along the cross-direction between the discrete chassis forming a first elastic belt and a second elastic belt; the chassis are subsequently folded; and the first and second elastic belts disposed on the chassis are bonded together to create a discrete diaper pant.

In one form, a process may be adapted for assembling disposable diaper pants, each diaper pant comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each diaper pant further comprising a ring-like elastic belt defined by a first elastic belt connected with the first waist region and second elastic belt connected with the second waist region, wherein opposing end regions of the first elastic belt are connected with opposing end regions of the second elastic belt to form a waist opening. The process includes the steps of: advancing a first continuous web in the machine direction; cutting the first continuous web into discrete chassis, wherein each chassis advances such that the longitudinal axis is parallel with the machine direction; spacing each chassis apart from each other along the machine direction; stretching a continuous elastic material in a machine direction; combining the elastic material with at least one nonwoven web to form a continuous elastic web having a first surface and an opposing second surface advancing in the machine direction; cutting the continuous elastic web into discrete elastic patches; turning each elastic patch such that the direction of stretch is substantially parallel with a cross direction, wherein each elastic patch has a leading end region and a trailing end region; connecting the first waist region of each chassis with a trailing end region of a first advancing elastic patch; connecting the second waist region of each chassis with a leading end region of a second advancing patch; cutting the each elastic patch to form a first elastic belt and a second elastic belt; folding each chassis; and connecting opposing end regions of each first elastic belt to opposing end regions of each second elastic belt to create discrete diaper pants.

In another form, a process may be adapted for assembling disposable diaper pants, each diaper pant comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each diaper pant further comprising a ring-like elastic belt defined by a first elastic belt connected with the first waist region and second elastic belt connected with the second waist region, wherein opposing end regions of the first elastic belt are connected with opposing end regions of the second elastic belt to form a waist opening. The process includes the steps of: advancing a first continuous web in the machine direction; advancing a continuous elastic web having a first surface and an opposing second surface in a machine direction; cutting the continuous elastic web into discrete elastic patches wherein the direction of stretch is substantially parallel with the machine direction; turning each elastic patch such that the direction of stretch is substantially parallel with a cross direction, wherein each elastic patch has a leading end region and a trailing end region; connecting each elastic patch with the first continuous web; simultaneously cutting each elastic patch and the first continuous web to form a first elastic belt, a second elastic belt, and discrete chassis; folding each chassis; and connecting opposing end regions of each first elastic belt to opposing end regions of each second elastic belt to create discrete diaper pants.

In yet another form, a process may be adapted for assembling disposable diaper pants, each diaper pant comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each diaper pant further comprising two first elastic belts connected with the first waist region and two second elastic belts each having proximal end portions connected with the second waist region, wherein distal end regions of the first elastic belts are connected with distal end regions of the second elastic belts to form a waist opening. The process includes the steps of: advancing a continuous web of chassis assemblies in the machine direction; advancing two continuous elastic webs in a machine direction, each elastic web having a first surface and an opposing second surface; cutting the continuous elastic webs into discrete elastic patches wherein the direction of stretch is substantially parallel with the machine direction; turning each elastic patch such that the direction of stretch is substantially parallel with a cross direction, wherein each elastic patch has a leading end region and a trailing end region; connecting each elastic patch with the continuous web of chassis assemblies; simultaneously cutting each elastic patch and the continuous length of chassis assemblies to form two first elastic belts, two second elastic belts, and discrete chassis; folding each chassis; and connecting distal end regions of each first elastic belt to distal end regions of each second elastic belt to create discrete diaper pants.

BRIEF DESCRIPTION OF THE DRAWINGS

FIG. 2A is a partially cut away plan view of the diaper pant shown in FIG. 1.

FIG. 2B is a partially cut away plan view of a second embodiment of a diaper pant.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 6A is a view of a continuous length of belt material from FIGS. 4 and 5 taken along line A-A FIG. 6B1 is a view of a discrete length of belt material from FIGS. 4 and 5 taken along line B1-B1.

FIG. 6B2 is a view of a discrete length of belt material from FIGS. 4 and 5 taken along line B2-B2.

FIG. 6C is a view of a continuous length of chassis assemblies from FIGS. 4, 5, and 8 taken along line C-C.

FIG. 6D is a view of a discrete chassis from FIG. 4 taken along line D-D.

FIG. 6E is a view of multiple discrete chassis spaced from each other along the machine direction MD connected with each other by the discrete lengths of belt material from FIG. 4 taken along line E-E.

FIG. 6F is a view of a discrete absorbent article advancing the machine direction MD from FIG. 4 taken along line F-F.

FIG. 6G is a view of a continuous length of chassis assemblies along the machine direction MD connected with discrete lengths of belt material from FIG. 5 taken along line G-G.

FIG. 6H is a view of a discrete absorbent article advancing in the machine direction MD from FIG. 5 taken along line H-H.

FIG. 6H1 shows an example of an absorbent article from FIG. 6H including curvilinear cross direction cuts between articles.

FIG. 6J is a view of two continuous lengths of belt material the machine direction MD from FIG. 8 taken along line J-J.

FIG. 6K is a view of a continuous length of chassis assemblies along the machine direction MD connected with discrete lengths of belt material from FIG. 8 taken along line K-K.

FIG. 6L is a view of a discrete absorbent article advancing in the machine direction MD from FIG. 8 taken along line L-L.

FIG. 7B1 is a view of a second embodiment of a discrete length of belt material from FIGS. 4 and 5 taken along line B1-B1.

FIG. 7B2 is a view of a discrete length of belt material from FIGS. 4 and 5 taken along line B2-B2.

FIG. 7B3 shows an alternative embodiment belt configuration from FIG. 7B2 including notched regions to define leg openings.

FIG. 7B4 shows an alternative embodiment belt configuration from FIG. 7B2 including an asymmetric notched configuration.

FIG. 7E is a view of multiple discrete chassis spaced from each other along the machine direction MD connected with each other by the second embodiment of discrete lengths of belt material from FIG. 4 taken along line E-E.

FIG. 7F is a view of a discrete absorbent article with the second embodiments of belt material advancing the machine direction MD from FIG. 4 taken along line F-F.

DETAILED DESCRIPTION OF THE INVENTION

Figure 1:
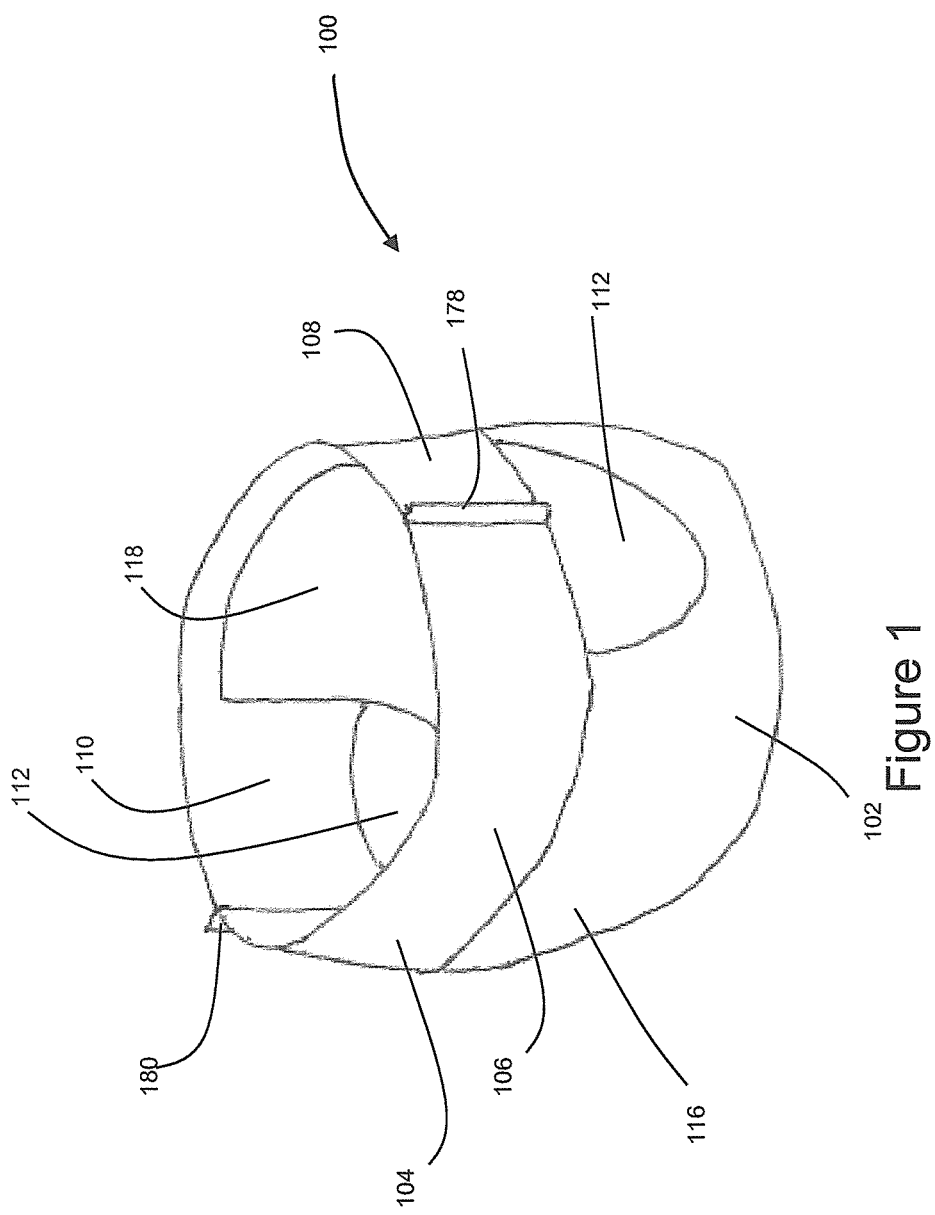
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. ⅒ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods for manufacturing absorbent articles, and in particular, methods for making diaper pants. As discussed in more detail below, diaper pants may include a chassis having a first waist region and a longitudinally opposed second waist region. The chassis may also include a longitudinal axis and a lateral axis, wherein the longitudinal axis extends through the first and second waist regions. Each diaper pant may further include a first elastic belt connected with the first waist region, and a second elastic belt connected with the second waist region. Opposing end regions of the elastic belts may be connected with each other to form a ring-like elastic belt. Aspects of the methods according to the present disclosure relate to the fabrication of diaper pants wherein discrete chassis are advanced in a machine direction such that the longitudinal axis is parallel with the machine direction. Discrete lengths of elastic belt materials are then connected with the first waist region of a first advancing chassis and the second waist region of a second advancing chassis. The lengths of elastic belt materials are cut along the cross-direction between the discrete chassis forming a first elastic belt and a second elastic belt; the chassis are subsequently folded; and the first and second elastic belts disposed on the chassis are bonded together to create a discrete diaper pant. This apparatus and process configuration forms a continuous web of articles formed by intermittently spaced chassis and intermittently spaced elastic belts bridging the gap between the intermittently spaced chassis. The spaced elastic belts may comprise one or more side panel portions and one or more waistband portions. The elastic material of the side panels may be continuous from one edge of the belt to the opposing edge or alternatively the elastic material of the side panels may be discontinuous from one edge of the belt to the opposing edge.

The following provides a general description of various types of diaper pants that may be produced with the methods and apparatuses disclosed herein to help provide additional context to the subsequent discussion of the process embodiments.

FIGS. 1 and 2A show an example of a diaper pant 100 that may be constructed in accordance with the methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, to allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn. Examples of extensible chassis configurations are disclosed in U.S. Pat. Nos. 5,968,029; 5,891,544; 5,723,087; 5,691,035; 5,518,801; 7,270,861; 6,830,800; and 5,993,432.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. patent application Ser. No. 12/434,984.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 116 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material 166 interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 side panels may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

It is to be appreciated that various embodiments of diaper pants can be manufactured according the methods disclosed herein, such as for example, the absorbent articles disclosed in U.S. Pat. No. 7,569,039, filed on Nov. 10, 2004, and U.S. Patent Publication No. 2005/0107764A1, filed on Nov. 10, 2004, both of which are hereby incorporated by reference herein.

Figure 4:
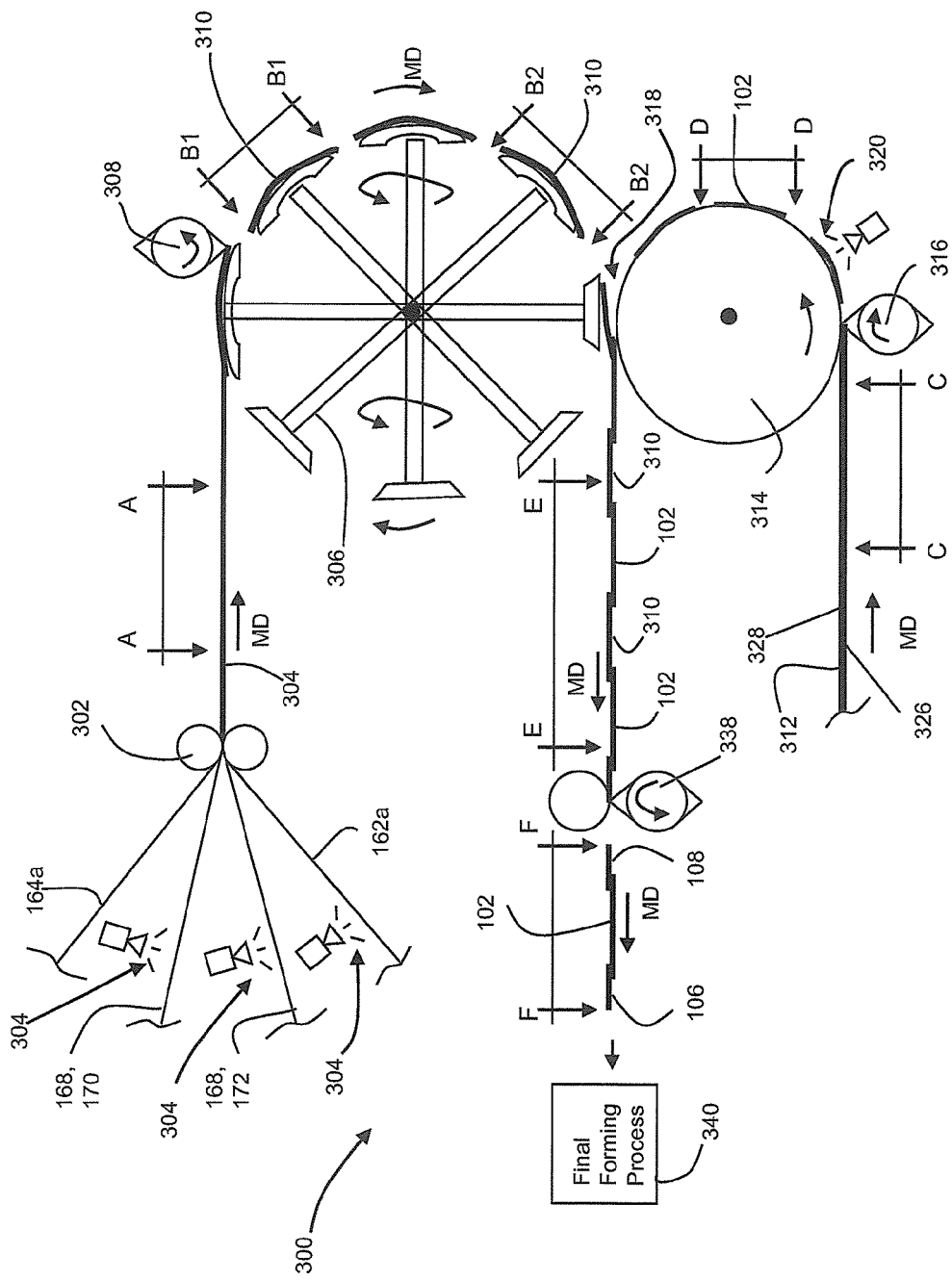
FIG. 4 is a schematic side view of a first converting apparatus adapted to manufacture diaper pants.

As previously mentioned, the apparatuses and methods according to the present disclosure may be utilized to assemble various components of diaper pants 100. For example, FIG. 4 shows a schematic view of a converting apparatus 300 adapted to manufacture diaper pants 100. The method of operation of the converting apparatus 300 may described with reference to the various components of diaper pants 100 described above and shown in FIGS. 1, 2A, 3A, and 3B. As described in more detail below, the converting apparatus 300 shown in FIG. 4 operates to advance discrete lengths of chassis 102 along a machine direction MD such that the longitudinal axis of each chassis 102 is parallel with the machine direction, and wherein the chassis 102 are spaced apart from each other along the machine direction. In addition, the apparatus 300 permanently connects first elastic belts 106 with the first waist regions 116 of advancing chassis 102 and permanently connects the second elastic belts 108 with the back waist regions 118 of advancing chassis 102.

As shown in FIGS. 4 and 6A, continuous lengths of outer layer belt material 162a, inner layer belt material 164a, outer elastic strands 170 and inner elastic strands 172 are advanced in a machine direction and combined at nip rolls 302 to form a continuous length of belt material 304. Before entering the nip rolls 302, the outer elastic strands 170 and inner elastic strands 172 are stretched in the machine direction. In addition, adhesive 306 may applied to the elastic strands 170, 172 as well as either or both of the continuous lengths of outer layer belt material 162a and inner layer belt material 164a before entering nip rolls 304. From the nip rolls 302 the continuous length of belt material 304 advances in the machine direction MD to a carrier apparatus 306. The elastic strands 170, 172, and thus, the continuous length of belt material 304 is maintained in a stretched condition along the machine direction while advancing to the carrier apparatus 306.

At the carrier apparatus 306, knife roll 308 cuts the continuous length of belt material 308 into discrete lengths or patches of belt material 310, such as shown in FIGS. 4 and 6B1. The carrier apparatus holds the discrete lengths of belt material 310 in the stretched state and rotates while at the same time changing the orientation of the advancing discrete lengths of belt material 310. The carrier apparatus 306 may also change the speed at which the chassis 102 advances in the machine direction MD. It is to be appreciated that various forms of carrier apparatus may be used with the methods herein, such as for example, the carrier apparatus disclosed in U.S. Pat. No. 7,587,966 and U.S. Pat. No. 6,620,276, which are incorporated herein by reference. FIG. 6B1 shows a first orientation of a discrete length of belt material 310 on the carrier apparatus 306 after initially being cut from the continuous length of belt material 304. As shown in FIG. 6B1, the discrete length of belt material 310 is oriented such that the elastic strands 170, 172 and the direction of stretch are substantially parallel with the machine direction MD. FIG. 6B2 shows a second orientation of the discrete length of belt material 310 before being removed from the carrier apparatus 306. As shown in FIG. 6B2, the discrete length of belt material 310 is oriented such that the elastic strands 170, 172 and the direction of stretch are substantially parallel with the cross direction CD. With the orientation shown in FIG. 6B2, each discrete length of belt material 310 includes a leading end portion 310a and a trailing end portion 310b. As discussed in more detail below, the discrete lengths of belt material 310 are transferred from the carrier apparatus 306 and combined with discrete chassis 102.

It is to be appreciated that in some embodiments, the belt material may not be kept in a stretched condition. For example, the belt material may be allowed to contract before being cut by the knife roll 308 transferred on the carrier apparatus 306. It should also be appreciated that the elastics strands 168 can be glued to the outer, garment facing layer 162 and the inner, wearer facing layer 164 in various ways, resulting in various elastic belt configurations. For example, glue may be applied intermittently to the elastic strands 168 such that when the continuous length of elastic belt material 304 is cut, end portions of the elastic strands 168 contract, resulting in uncontracted opposing end portions of the discrete lengths of elastic belts 310. In other example, the elastic strands 168 may be glued such that only end portions of the elastics 168 in the discrete lengths of elastic belt material 310 are bonded to the outer, garment facing layer 162 and the inner, wearer facing layer 164. As such, extension of the side panels can extend and impart tension to the elastic strands 168 independent of the chassis.

As shown in FIGS. 4 and 6C, a continuous length of chassis assemblies 312 are advanced in a machine direction MD to a carrier apparatus 314 and cut into discrete chassis 102 with knife roll 316. The continuous length of chassis assemblies may include absorbent assemblies 140 sandwiched between topsheet material 138 and backsheet material 136. The absorbent assemblies 140 may be spaced apart from each other along the machine direction MD. A portion of the chassis assembly is cut-away to show a portion of the topsheet material 138 and an absorbent assembly 140. As shown in FIG. 4, the discrete chassis 102 are spaced from each other in the machine direction by the carrier apparatus 314. An example carrier apparatus 318 for achieving the spacing between discrete components is disclosed in disclosed in U.S. Pat. No. 7,587,966 and U.S. Pat. No. 6,620,276. FIG. 6D shows the orientation of a chassis 102 advancing on the carrier apparatus 314, wherein the longitudinal axis 124 of the chassis 102 is generally parallel with the machine direction MD. While the chassis 102 shown in FIG. 6D is shown with the first laterally extending end edge 144 as a leading edge and the second laterally extending end edge 146 as the trailing edge, it is to be appreciated that in other embodiments, the chassis 102 may be advanced in other orientations. For example, the chassis may be oriented such that the first laterally extending end edge 144 is a trailing edge and the second laterally extending end edge 146 is a leading edge.

As shown in FIG. 4, the carrier apparatus 314 advances the discrete chassis 102 to a nip 318 between the between the carrier apparatus 306 and the carrier apparatus 314. At the same time, the carrier apparatus 306 advances discrete lengths of belt material 310 to the nip 318, where each discrete length of belt material 310 is connected with two discrete chassis 102. Before entering nip 318, adhesive 320 may be intermittently applied to the chassis 102 in locations to be bonded with the discrete lengths of belt material 310. It should be appreciated that instead of in addition to applying adhesive 320 to the chassis 102, adhesive may be applied to the discrete lengths of belt material 310 on the carrier apparatus 306. With particular reference to FIGS. 4, 6B2, 6D, and 6E, the leading end portion 310a of each discrete length of belt material 310 is connected with a trailing end portion adjacent the second laterally extending end edge 146 of an advancing chassis 102. And the trailing end portion 310b of each discrete length of belt material 310 is connected with a leading end portion adjacent the first laterally extending end edge 144 of a subsequently advancing chassis 102. As such, opposing end portions of each discrete length of belt material 310 are connected with two chassis 102 traveling in the machine direction, such as shown in FIG. 6E.

From the nip 318, the interconnected lengths of belt material 310 and chassis 102 advance to a knife roll 338 where the discrete belt material 310 regions 336 are cut along the cross direction to create the first elastic belt 106 on an absorbent article 100 and the second elastic belt 108 on a subsequently advancing absorbent article 100. As shown in FIGS. 6E and 6F, the belt material 310 may be cut in the cross direction in a space between waist elastic strands 170.

As shown in FIG. 4, after knife roll 338, the absorbent articles may advance to final forming processes 340. Such final forming processes may includes folding the chassis of the absorbent articles and bonding or seaming the first end region 106a of the first elastic belt 106 with the first end region 108a of the second elastic belt 108, and bonding or seaming the second end region 106b of the first elastic belt 106 with the second end region 108b of the second elastic belt 108. Example processes and apparatuses for carrying out such folding and seaming processes are disclosed in U.S. Pat. Nos. 5,779,831; and 6,113,717; and U.S. Patent Publication Nos. 2008/0083489A1; 2009/0098995A1; and 2009/0094941A1 all of which are incorporated herein by reference. As such, depending on the final forming process configuration, the side seams 178, 180 may in the form of a butt seam or an overlapping seam. Other final forming processes may include side panel tucking, such as disclosed in U.S. Provisional Patent Application Nos. 61/322,349 and 61/322,338, both filed on Apr. 9, 2010; as well as U.S. Pat. Nos. 6,723,035 and 6,776,316, all incorporated herein by reference.

As previously mentioned, the bonds of the side edge seams 178 and 180 may be permanent or refastenable and can be formed in various ways appropriate for the specific materials employed. Thus, the side seams may be formed in various ways, such as for example, with heat bonds, pressure welds, adhesives, cohesive bonds, and/or mechanical fasteners. Example bond types may include discrete bonds such as sonic sealed bonds, heat sealed bonds, high pressure bonds, radio frequency bonds, adhesive or cohesive bonds, sewed bonds, autogeneous bonds, and combinations thereof. In accordance with one aspect of the disclosure, the side seams 178 and 180 may be joined by a predetermined pattern of heat/pressure or ultrasonic welds which withstands the forces and stresses exacted onto the side edge seam during application and wear of the pant. The permanent side edge seams 178, 180 may be formed as disclosed in U.S. Pat. Nos. 5,779,831; 5,772,825; 5,607,537; 5,622,589; 5,662,638; 6,042,673; and 6,726,792.

It is to be appreciated that the converting apparatus 300 described above can be configured to construct and utilize different shapes and sizes of discrete lengths of belt material 310. For example, the knife roll 308 can be configured to cut the continuous length of belt material 308 into discrete lengths of belt material 310, such as shown in FIGS. 4 and 7B1. As shown in FIG. 7B1, the discrete lengths of belt material 310 are cut into an I-shape wherein notches of material and partial lengths of inner elastics 172 are removed. As such, notched regions 311 of the discrete length of belt material 310 separate opposing pluralities 173 of inner elastics 172. As shown in FIG. 7B1, the discrete length of belt material 310 is oriented such that the elastic strands 170, 172 and the direction of stretch are substantially parallel with the machine direction MD. FIG. 7B2 shows a second orientation of the discrete length of belt material 310 before being removed from the carrier apparatus 306. As shown in FIG. 7B2, the discrete length of belt material 310 is oriented to resemble a H-shape with respect to the machine direction MD such that the elastic strands 170, 172 and the direction of stretch are substantially parallel with the cross direction CD. With the orientation shown in FIG. 7B2, each discrete length of belt material 310 includes a leading end portion 310*a* and a trailing end portion 310*b*. It is to be appreciated that the belt material may be cut to define various types of shapes. For example, FIG. 7B3 shows an embodiment wherein the belt material includes notched regions 198 to define leg openings. In another example, FIG. 7B4 shows an asymmetric notched region 199 configuration.

As shown in FIGS. 7E and 7F, the discrete lengths of belt material 310 are transferred from the carrier apparatus 306 and combined with discrete chassis 102 at nip 318. From the nip 318, the interconnected lengths of belt material 310 and chassis 102 advance to a knife roll 338 where the discrete belt material 310 regions 336 are cut along the cross direction to create the first elastic belt 106 on an absorbent article 100 and the second elastic belt 108 on a subsequently advancing absorbent article 100. The belt material 310 may be cut in the cross direction in a space between waist elastic strands 170. As shown in FIGS. 7E and 7F, the waist elastic strands 170 extend completely laterally across the longitudinal axis 124 of the chassis, whereas the inner elastic strands 172 of the first elastic belt 106 and the second elastic belt 108 do not extend completely across the longitudinal axis 124 of the chassis 102.

Figure 5:
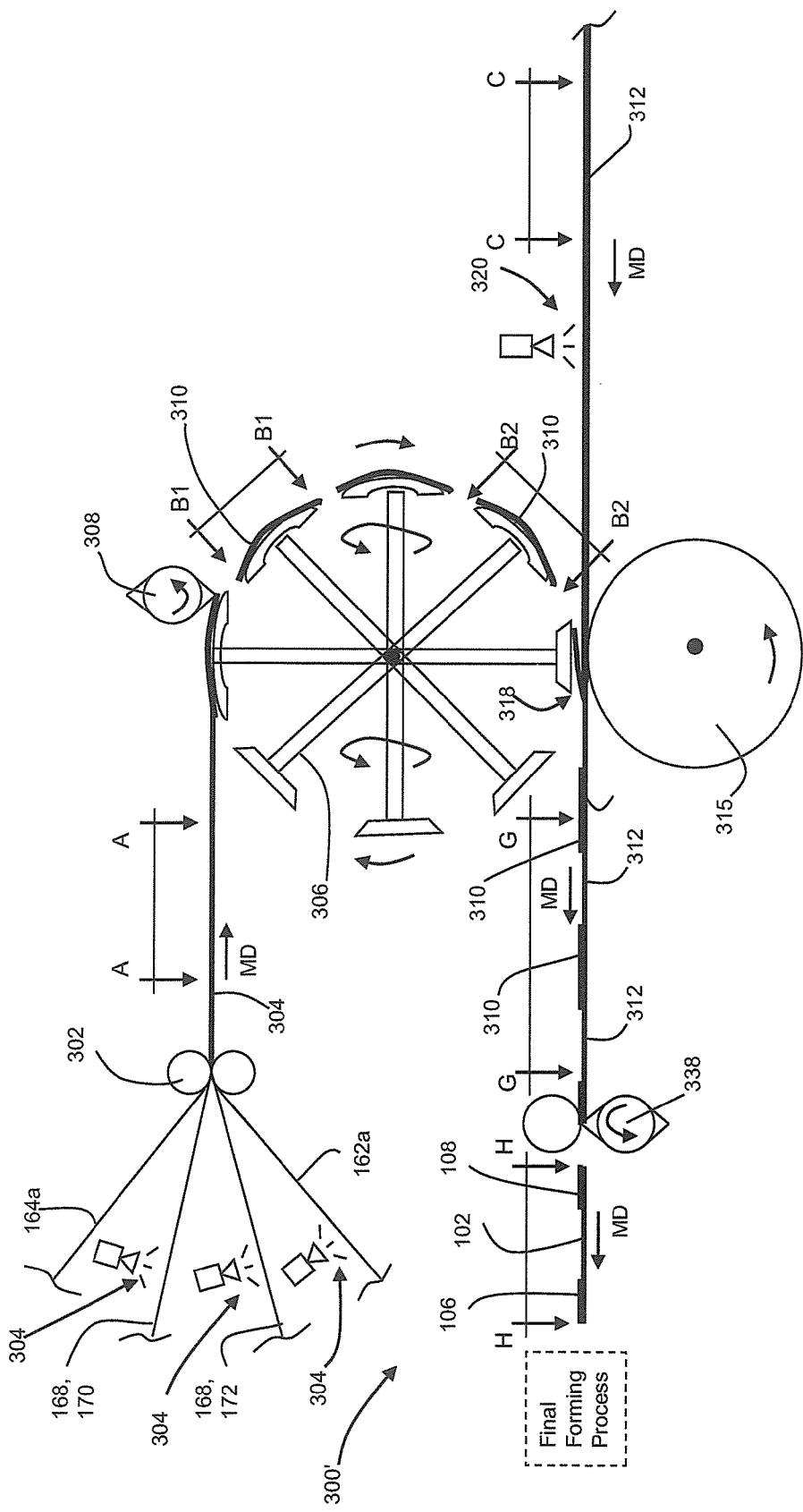
FIG. 5 is a schematic side view of a second converting apparatus adapted to manufacture diaper pants.

FIG. 5 shows a schematic view of a second embodiment of a converting apparatus 300' adapted to manufacture pant diapers 100, such as shown in FIG. 2B. As discussed in more detail below, the method of operation of the converting apparatus 300' differs from the converting apparatus described above with respect to FIG. 4 with respect to the connection of two separate and discrete lengths of belt material 310 with a continuous length of chassis assemblies 312. Other aspects of the assembly process shown in FIG. 5 are the same as described above with reference to FIGS. 3, 6A, 6B1, 6B2, and 6C. It is also to be appreciated that converting apparatus 300' of FIG. 5 can be configured to create and apply the elastic belt material 310 described above with respect to FIGS. 7B1 and 7B2. Also, as discussed above, extensible chassis configurations can be utilized, examples of which are disclosed in U.S. Pat. Nos. 5,968,029; 5,891,544; 5,723,087; 5,691,035; 5,518,801; 7,270,861; 6,830,800; and 5,993,432.

With reference to FIGS. 5 and 6C, a continuous length of chassis assemblies 312 are advanced in a machine direction MD to a nip 318 between the between the carrier apparatus 306 and a roll 315. At the same time, the carrier apparatus 306 advances discrete lengths of belt material 310 to the nip 318, where discrete lengths of belt material 310 are connected to the continuous length of chassis assemblies 312. As shown in FIG. 6G, the discrete lengths of belt material 310 are spaced apart from each other along the machine direction MD. Before entering nip 318, adhesive 320 may be intermittently applied to the continuous length of chassis assemblies 312 in locations to be bonded with the continuous length of chassis assemblies 312. It should be appreciated that instead of or in addition to applying adhesive 320 to the continuous length of chassis assemblies 312, adhesive may be applied to the discrete lengths of belt material 310 on the carrier apparatus 306.

From the nip 318, the connected lengths of belt material 310 and the continuous length of chassis assemblies 312 advance to a knife roll 338 where the discrete belt material 310 regions 336 are cut along the cross direction to create the first elastic belt 106 on an absorbent article 100 and the second elastic belt 108 on a subsequently advancing absorbent article 100. As shown in FIGS. 6G and 6H, the belt material 310 and the continuous length of chassis assemblies 312 may be cut in the cross direction in a space between waist elastic strands 170. As shown in FIG. 5, after knife roll 338, the absorbent articles may advance to final forming processes 340, such as described above. It is to be appreciated that the belt material 310 and the continuous length of chassis assemblies 312 may be cut in the cross direction along a curvilinear line in a space between waist elastic strands 170, such as shown for example in FIG. 6H1, which shows a curvilinear first laterally extending end edge 144*a* and a curvilinear second laterally extending end edge 146*a*. Other example cut lines are shown and described in U.S. Pat. Nos. 7,361,167 and 7,828,783. Further, the cross directional cut need not be in a space between waist elastic bands, but instead, may also cut through some elastics.

Figure 8:
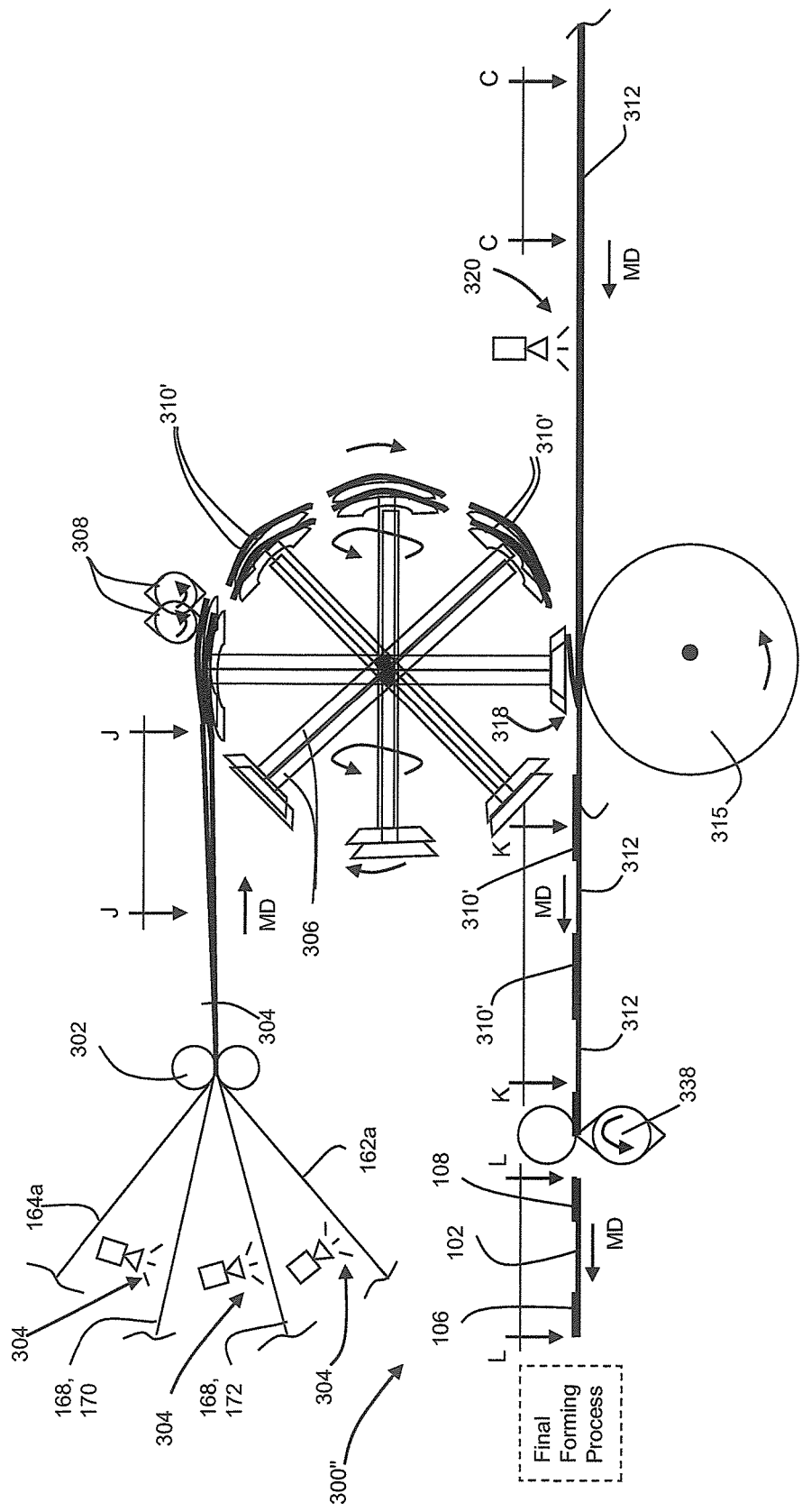
FIG. 8 is a schematic side view of a third converting apparatus adapted to manufacture diaper pants.

FIG. 8 shows a schematic view of a third embodiment of a converting apparatus 300" adapted to manufacture pant diapers 100. As discussed in more detail below, the method of operation of the converting apparatus 300" differs from the converting apparatus described above with respect to FIG. 5 in that two discrete front belts 106' and two discrete back belts 108' are connected with a continuous length of chassis assemblies 312.

With reference to FIGS. 8 and 6J, two continuous lengths of belt material 304 are advanced in a machine direction MD to two respective carrier apparatuses 306, wherein two knife rolls 308 cut the continuous lengths of belt material 308 into discrete lengths of belt material 310'. The two carrier apparatuses operate to advance the discrete lengths of belt material 310' to the nip 318 as discussed above with reference to FIG. 5. And the discrete lengths of belt material are connected with the continuous length of chassis assemblies 312. As shown in FIG. 6K, the discrete lengths of belt material 310' are spaced apart from each other along the machine direction MD and the cross direction CD. From the nip 318, the connected lengths of belt material 310' and the continuous length of chassis assemblies 312 advance to a knife roll 338 where the discrete belt material 310' regions 336 are cut along the cross direction to create two first elastic belts 106' on an absorbent article 100 and two the second elastic belts 108' on a subsequently advancing absorbent article 100. As shown in FIGS. 6K and 6L, the belt material 310' and the continuous length of chassis assemblies 312 may be cut in the cross direction in a space between waist elastic strands 170. As shown in FIG. 8, after knife roll 338, the absorbent articles may advance to final forming processes 340, such as described above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for assembling disposable diaper pants, each diaper pant comprising a chassis having a first waist region longitudinally opposed to a second waist region, and having a longitudinal axis and a lateral axis, the chassis comprising: a topsheet, a backsheet, and an absorbent core disposed between the topsheet and the backsheet, each diaper pant further comprising a ring-like elastic belt defined by a first elastic belt connected with the first waist region and second elastic belt connected with the second waist region, wherein opposing end regions of the first elastic belt are connected with opposing end regions of the second elastic belt to form a waist opening, the process comprising the steps of:
    advancing a first continuous web in the machine direction;
    cutting the first continuous web into discrete chassis, wherein each chassis advances such that the longitudinal axis is parallel with the machine direction;
    spacing each chassis apart from each other along the machine direction;
    stretching a continuous elastic material in a machine direction;
    combining the elastic material with at least one nonwoven web to form a continuous elastic web having a first surface and an opposing second surface advancing in the machine direction;
    cutting the continuous elastic web into discrete elastic patches;
    turning each elastic patch such that the direction of stretch is substantially parallel with a cross direction, wherein each elastic patch has a leading end region and a trailing end region;
    connecting the first waist region of each chassis with the trailing end region of a first advancing elastic patch;
    connecting the second waist region of each chassis with the leading end region of a second advancing patch;
    cutting the each elastic patch to form the first elastic belt and the second elastic belt;
    folding each chassis; and
    connecting opposing end regions of each first elastic belt to opposing end regions of each second elastic belt to create discrete diaper pants.

2. The process of claim 1, the elastic material comprises outer, waist elastic strands and inner, waist elastic strands.

3. The process of claim 2, further comprising the step of removing notches of material and removing portions of lengths of the inner, waist elastic strands from the discrete elastic patches such that the discrete elastic patches define an I-shape.

4. The process of claim 3, wherein the inner, waist elastic strands do not extend across the longitudinal axis.

5. The process of claim 2, further comprising the step of removing notched regions of material from the discrete elastic patches to define leg openings.

6. The process of claim 1, wherein the first waist region is a front waist region.

7. The process of claim 1, wherein the second waist region is a back waist region.

* * * * *